United States Patent
Sater

(10) Patent No.: US 7,597,703 B2
(45) Date of Patent: Oct. 6, 2009

(54) MECHANICALLY EXPANDABLE OCCLUDER

(75) Inventor: Ghaleb A Sater, Lynnfield, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 405 days.

(21) Appl. No.: 10/935,851

(22) Filed: Sep. 7, 2004

(65) Prior Publication Data

US 2006/0052814 A1    Mar. 9, 2006

(51) Int. Cl.
*A61M 29/00* (2006.01)
(52) U.S. Cl. .................................... 606/198
(58) Field of Classification Search .............. 606/110, 606/113, 114, 127, 159, 191, 200, 213, 198, 606/72, 194; 128/887; D24/162; 604/105, 604/106
See application file for complete search history.

(56) References Cited

U.S. PATENT DOCUMENTS

| | | | | |
|---|---|---|---|---|
| 3,397,699 A | * | 8/1968 | Kohl | 604/105 |
| 3,667,474 A | * | 6/1972 | Lapkin et al. | 606/198 |
| 4,585,000 A | * | 4/1986 | Hershenson | 606/194 |
| 4,794,928 A | | 1/1989 | Kletschka | |
| 4,990,156 A | | 2/1991 | Lefebvre | |
| 5,197,971 A | * | 3/1993 | Bonutti | 606/192 |
| 5,267,554 A | * | 12/1993 | Wilk | 600/224 |
| 5,358,496 A | | 10/1994 | Ortiz et al. | 606/198 |
| 5,626,605 A | | 5/1997 | Irie et al. | |
| 5,645,589 A | | 7/1997 | Li | 623/16 |
| 5,843,127 A | | 12/1998 | Li | 606/232 |
| 5,855,565 A | | 1/1999 | Bar-Cohen et al. | 604/104 |
| 6,022,373 A | * | 2/2000 | Li | 606/232 |
| 6,129,762 A | * | 10/2000 | Li | 623/13.11 |
| 6,306,163 B1 | * | 10/2001 | Fitz | 623/1.12 |
| 6,312,407 B1 | | 11/2001 | Zadno-Azizi et al. | |
| 6,398,798 B2 | * | 6/2002 | Selmon et al. | 606/159 |
| 6,511,496 B1 | * | 1/2003 | Huter et al. | 606/200 |
| 6,537,296 B2 | * | 3/2003 | Levinson et al. | 606/200 |
| 6,540,722 B1 | * | 4/2003 | Boyle et al. | 604/106 |
| 6,558,405 B1 | * | 5/2003 | McInnes | 606/200 |
| 2003/0045898 A1 | | 3/2003 | Harrison et al. | |

FOREIGN PATENT DOCUMENTS

EP    0309078 A2    3/1989

* cited by examiner

*Primary Examiner*—Anhtuan T Nguyen
*Assistant Examiner*—Ryan J Severson

(57) ABSTRACT

An occluder catheter having an outer tube, an inner shaft extending slidably through the outer tube, and two expanders attached, respectively, to the distal ends of the inner shaft and the outer tube. The expanders each have a plurality of circumferentially spaced, longitudinally oriented fingers. The fingers each have radially expandable ends and radially constrained ends and the fingers of each expander are interposed with the fingers of the other expander. A flexible non-porous sleeve covers at least the fingers of both expanders. By moving the outer tube with respect to the inner shaft, the occluder is transformable between a collapsed configuration and an expanded configuration wherein the fingers of at least one of the expanders are radially splayed to dilate the sleeve. One embodiment of the invention incorporates a single expander having circumferentially juxtaposed fingers, the expander being mated with a deflector ring.

9 Claims, 3 Drawing Sheets

MECHANICALLY EXPANDABLE OCCLUDER

FIELD OF THE INVENTION

The present invention relates generally to intraluminal devices for capturing particulates in a vessel of a patient. More particularly, the invention relates to an occluder for capturing emboli in a vessel during an interventional vascular procedure. Furthermore, the invention concerns an occluder mounted on a guidewire that can also be used to direct an interventional catheter to a treatment site within a patient.

BACKGROUND OF THE INVENTION

Various intervention techniques have been developed to treat narrowings in blood vessels, allowing increased blood flow through the vessels. One technique for treating stenosis or occlusion of a blood vessel is balloon dilatation, or percutaneous transluminal angioplasty (PTA). Generally, an arterial sheath is introduced through a puncture or incision in the patient's skin to provide percutaneous access to blood vessels. This is followed by insertion of a balloon catheter through the arterial sheath and its advancement through the blood vessels to the target site, where the stenosis is then dilated. PTA catheters are commonly guided through blood vessels by thin wires called guidewires, which may be either solid or hollow. To provide radial support to the treated vessel in order to prolong the positive effects of PTA, a stent may be implanted in conjunction with the procedure.

Thrombectomy is a minimally invasive technique for removal of an entire thrombus or a sufficient portion of the thrombus to enlarge the stenotic or diseased blood vessel and may be accomplished instead of a PTA procedure. Atherectomy is another well-known minimally invasive procedure that mechanically cuts or abrades a stenosis within the diseased portion of the vessel. Alternatively, ablation therapies use laser or RF signals to superheat or vaporize a thrombus within the vessel.

During each of these procedures, there is a risk that emboli dislodged by the procedure will migrate through the circulatory system and cause ischaemic events, such as infarction or stroke. Thus, clinicians have approached prevention of escaped emboli through use of occlusion devices, filters, lysing, and aspiration techniques. For example, it is known to remove the embolic material by suction through an aspiration lumen in the treatment catheter or by capturing emboli in a filter or occlusion device positioned distal of the treatment area.

A difficulty associated with combing angioplasty with embolic protection is the limited time available to perform the procedure. That is, in order to contain emboli produced during intravascular therapy, the vessel is generally occluded, meaning that no blood perfuses through the vessel to the end organ. Thus, depending upon the patient's vasculature and the organ involved, the complete procedure may need to be completed within just a few minutes.

Known embolic protection guidewires comprise an inflatable occlusion balloon located adjacent the distal end of a hollow guidewire. Dilute radiopaque contrast liquid is forced through the guidewire lumen to inflate and deflate the occlusion balloon. However, operating the balloon may take longer than desired due to the viscosity of the inflation medium, the small size of the inflation lumen, and the requirement to attach, detach and operate one or more inflation accessories at the proximal end of the guidewire.

U.S. Pat. No. 6,312,407 B1 teaches mechanically operated occlusion devices that may function more quickly than occlusion balloons, thus saving time during the treatment procedure. However, some mechanical occluder designs are complex and costly to produce. Accordingly, there is a need for a simplified occluder device that provides containment of emboli and other particulates.

SUMMARY OF THE INVENTION

The present invention provides an occluder catheter having a hollow outer tube, and an inner shaft extending slidably through the outer shaft. Two expanders are attached, respectively, to the distal ends of the inner shaft and the outer tube. The expanders each have a plurality of circumferentially spaced, longitudinally oriented fingers. The fingers have radially expandable ends and radially constrained ends and the fingers of each expander are interposed with the fingers of the other expander. A flexible non-porous sleeve covers at least the fingers of both expanders. The occluder is transformable between a collapsed configuration and an expanded configuration wherein the fingers of at least one of the expanders are radially splayed to dilate the sleeve.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof. The accompanying drawings are not to scale.

DETAILED DESCRIPTION OF THE INVENTION

Figure 1:
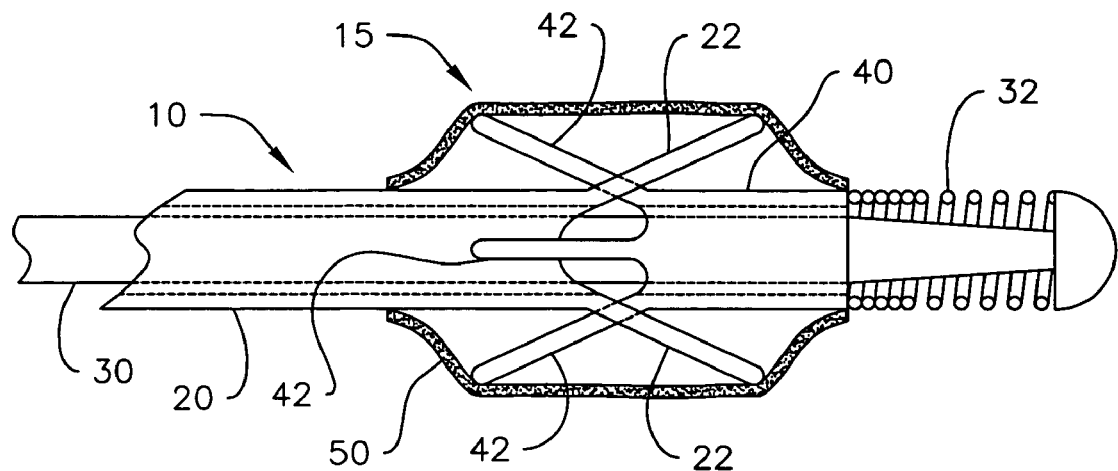
FIG. 1 illustrates a distal portion of an occluder guidewire in accordance with the invention, shown in the expanded configuration and partially sectioned for clarity.

Although the following description of the invention relates to the capture of embolic material that may be dislodged during vascular interventions, it is to be understood that the invention is applicable to other procedures in which the user desires to occlude a tubular body vessel, either temporarily or permanently. In FIG. 1, occluder guidewire 10 includes outer tube 20 and inner shaft 30 that extends slidably through and extends from outer tube 20. Flexible tubular tip member 32, such as a coil spring, is fixed around the tapered distal end of inner shaft 30.

Distal expander 40 is coupled to inner shaft 30, and has a tubular body with a plurality of fingers 42 that are longitudinally oriented and circumferentially spaced about the proximal end of expander 40. Fingers 42 have radially expandable proximal ends or tips, and radially constrained distal ends that are formed as an integral proximal portion of the tubular body of distal expander 40. A proximal expander comprises a plurality of fingers 22 that are longitudinally oriented and circumferentially spaced about, and formed as an integral distal portion of, outer tube 20. Fingers 22 have radially expandable distal ends or tips, and radially constrained proximal ends. The proximal and distal expanders are longitudinally aligned in a slidable, mating arrangement such that fingers 22 and 42 are interposed with each other. Sleeve 50 is mounted about the proximal and distal expanders to cover at least fingers 22 and 42.

Figure 2:
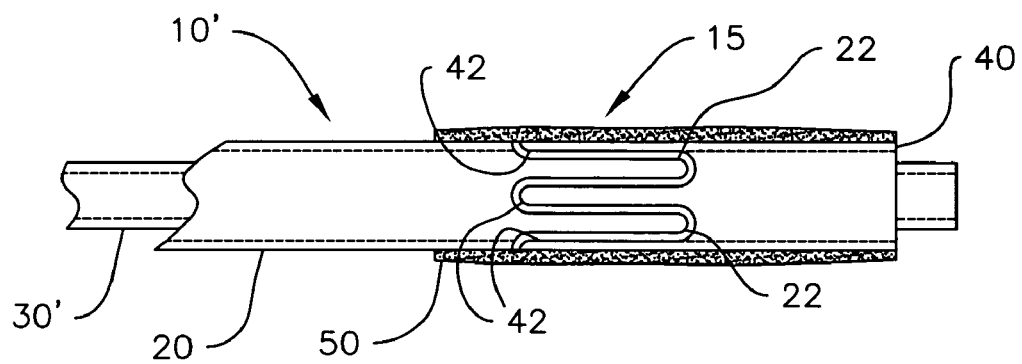
FIG. 2 illustrates a distal portion of an occluder catheter in accordance with the invention, shown in the collapsed configuration and partially sectioned for clarity.

Relative longitudinal movement between the proximal and distal expanders accompanies a transformation of occluder 15 between an expanded configuration, as shown in FIG. 1, and a collapsed configuration shown in FIG. 2. The operative longitudinal movement between the proximal and distal expanders is achieved by pulling or pushing outer tube 20 with respect to inner shaft 30. Such action may be accomplished, if desired, by use of a removable accessory handle (not shown) that grips and manipulates proximal portions of outer tube 20 and inner shaft 30 outside the patient. Sliding the proximal and distal expanders toward each other forces fingers 22 and 42 into greater interposition and splays the radially expandable finger ends of at least one expander, thus dilating sleeve 50 into sealing engagement with the patient's vessel. In the expanded configuration, sleeve 50 can occlude fluid flow because it is formed of non-porous material. Sliding the proximal and distal expanders apart allows occluder 15 to return to the collapsed configuration wherein fingers 22 and 42 are less interposed, and may form a hollow cylinder, as shown in FIG. 2.

Occluder guidewire 10 may be sized for directing catheters to a targeted treatment location. For example, outer tube 20 may be thin walled tubing having an outer diameter of 0.014 in (0.0006 mm) for directing catheters in coronary or cerebral arteries, or in other small caliber vessels. Treatments in larger target vessels may require outer tube 20 to have a larger outer diameter for guiding relatively larger therapy catheters. Outer tube 20 may be formed of metals such as stainless steel or TiNi (nitinol) or of a high modulus polymer such as thermoset polyimide.

Inner shaft 30 may be a solid core wire or a combination of tubing and wire made of a metal such as stainless steel or TiNi (nitinol). FIG. 2 shows occluder catheter 10', which is similar to occluder guidewire 10, except that inner shaft 30' is a hollow tube having a guidewire lumen there through.

Sleeve 50 may be made from a natural rubber, a synthetic rubber, a thermoplastic elastomer, a styrenic thermoplastic elastomer, a styrene-butylene-styrene, an inelastic thermoplastic, a polyester, a polyamide, a polyolefin, and a block co-polymer, a blend, a lamination, or a combination of the above materials. Sleeve 50 may be made of an elastic material and fitted snugly about the collapsed expander elements to provide a low crossing profile. Sleeve 50 may also be made of an inelastic material and folded about the collapsed expander elements similar to a deflated angioplasty balloon. Sleeve 50 is adhered, at its distal and proximal ends, to occluder guidewire 10 or occluder catheter 10'. Sleeve 50 is long enough and its bonds are spaced apart sufficiently so as not to obstruct the maximum interposition of fingers 22 and 42 as occluder 15 reaches the expanded configuration. The minimum length of sleeve 50 also ensures that spaces between fingers 22 and 42 are covered to prevent leakage of potentially contaminated fluid through expanded occluder 15. Sleeve 50 may be bonded to the underlying portions of guidewire 10 or occluder catheter 10' using known adhesives and techniques. The distal end of sleeve 50 may be attached to either distal expander 40 or to tip member 32.

Figure 3:
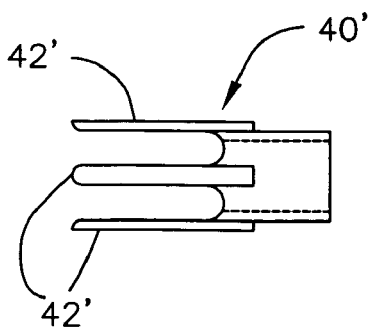
FIG. 3 illustrates an alternative expander for an occluder in accordance with the invention.

An integrally formed expander may be cut from stainless steel, TiNi or other metal tubing using known techniques such as laser machining or electrical discharge machining (EDM). Alternatively, the expander may be cut from a flat metal sheet, then rolled up and joined at the edges to form a tube. Alternatively, FIG. 3 illustrates expander 40' formed by attaching separately formed fingers 42' to a tubular body, as by welding, soldering, or gluing. Fingers 42 and 42' are shown with parallel sides, but alternative finger shapes may also be useful.

Figure 4:
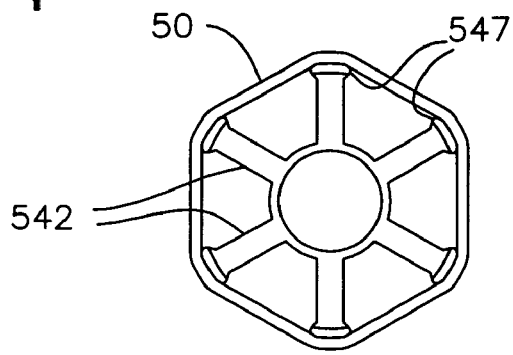
FIG. 4 is a transverse cross-section of an expander and sleeve for another occluder in accordance with FIGS. 5 and 6, shown in an expanded configuration.
Figure 5:
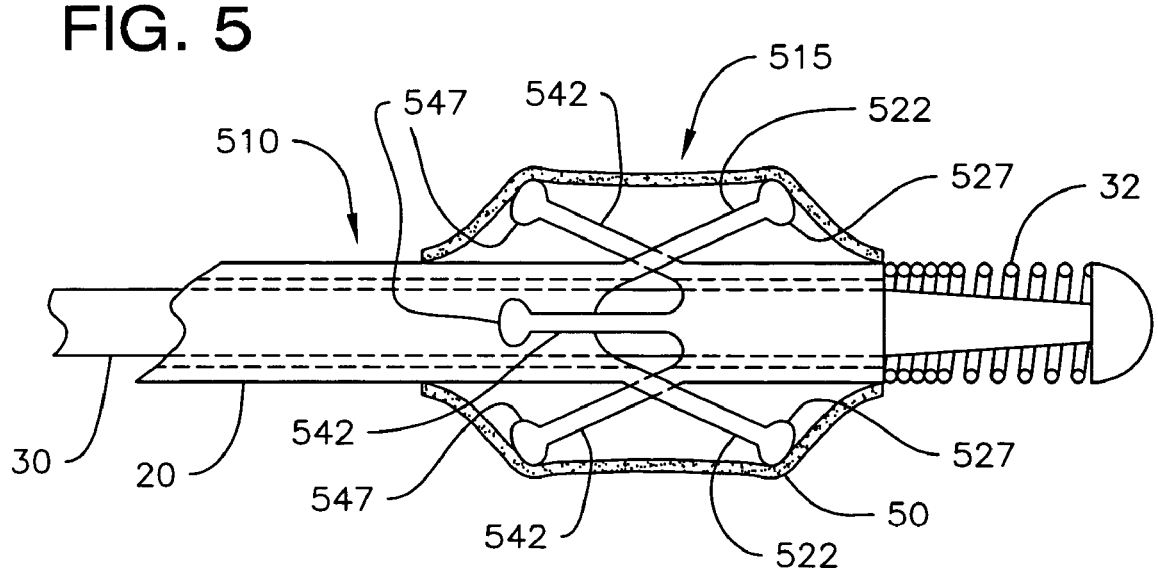
FIG. 5 illustrates a distal portion of another occluder guidewire in accordance with the invention, shown in the expanded configuration and partially sectioned for clarity.

FIGS. 4 and 5 illustrate occluder guidewire 510, which is similar to occluder guidewire 10, except that fingers 522, 542 are wider at their radially expandable ends 527, 547 than at their radially constrained ends. The finger widths may taper gradually over their lengths (not shown), or their radially expandable ends may simply have broad, paddle-shaped ends 527, 547, as illustrated in FIG. 5. Wide finger ends 527, 547 have larger surface contact with sleeve 50. Wide finger ends 527, 547 support better sealing contact between sleeve 50 and the vessel wall. Wide finger ends 527, 547 may also reduce any risk of fingers 522, 542 perforating sleeve 50.

Figure 6:
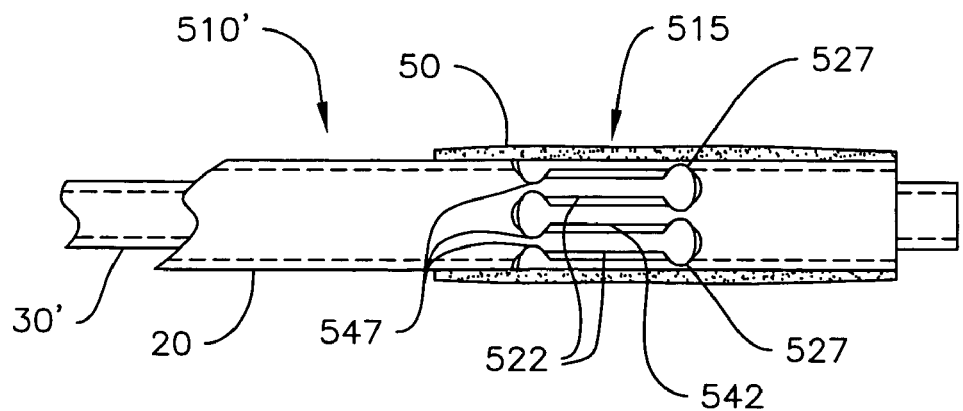
FIG. 6 illustrates a distal portion of another occluder catheter in accordance with the invention, shown in the collapsed configuration and partially sectioned for clarity.

FIG. 6 shows occluder catheter 510', which is similar to occluder guidewire 510, except that inner shaft 30' is a hollow tube having a guidewire lumen there through. Similar to operation of occluder guidewire 510, sliding the proximal and distal expanders toward each other forces fingers 522, 542 into greater interposition and splays the radially expandable finger ends of at least one expander, thus dilating sleeve 50 into sealing engagement with the patient's vessel. In addition, sliding the proximal and distal expanders apart allows occluder 515 to return to the collapsed configuration wherein fingers 522, 542 are less interposed.

As shown in FIG. 6, when occluder 515 is in the collapsed configuration, paddle-shaped ends 527, 547 may be too wide to fit into the slots between interposing fingers 522, 542. Instead, paddle-shaped ends 527, 547 rest on the outer surface of adjacent fingers 522, 542. The resulting double-thickness at finger ends 527, 547 causes the collapsed configuration of occluder 515 to have a slightly larger collapsed profile than that of occluder 15. However, by resting above the slots, finger ends 527, 547 will easily begin the required sliding motion to expand and dilate sleeve 50 as described above. In comparison, to begin expansion of occluder 15, the ends of fingers 22, 42 need to overcome an initial step to escape the slots and begin sliding toward the expanded configuration. To facilitate this movement, the step may include a radius, a tapered ramp or a chamfer formed at the tips of fingers 22, 42, 42' (see FIG. 3), or at the base of each slot there between.

Figure 7:
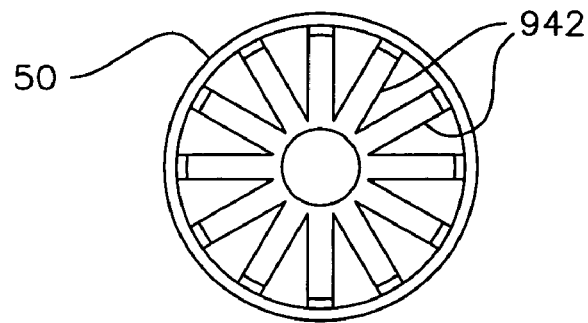
FIG. 7 is a transverse cross-section of an expander and sleeve for yet another occluder in accordance with FIGS. 8 and 9, shown in an expanded configuration.
Figure 8:
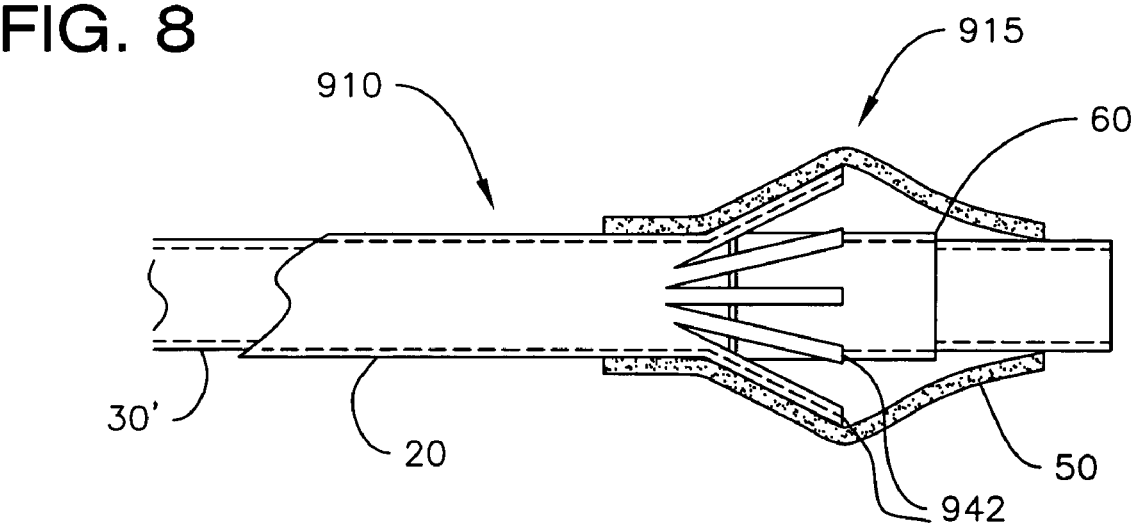
FIG. 8 illustrates a distal portion of yet another occluder guidewire in accordance with the invention, shown in the expanded configuration and partially sectioned for clarity.
Figure 9:
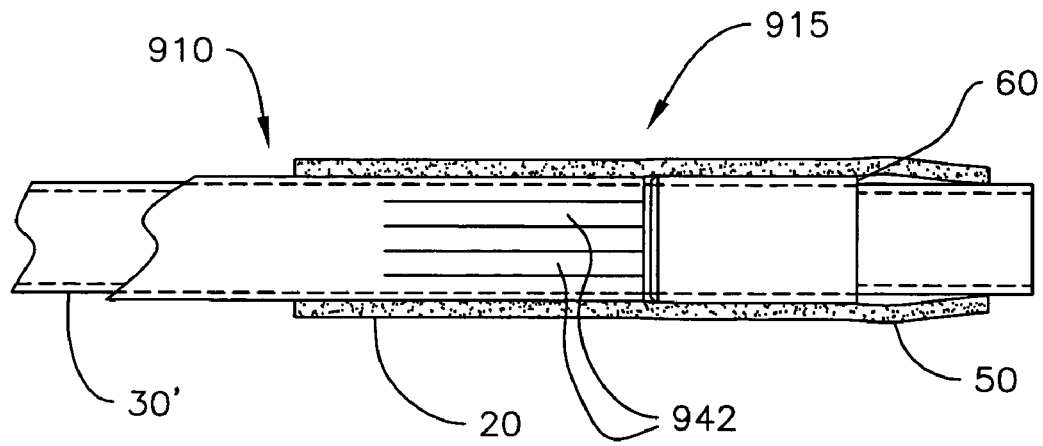
FIG. 9 illustrates a distal portion of yet another occluder catheter in accordance with the invention, shown in the collapsed configuration and partially sectioned for clarity.

In the expanded configurations of occluders 15 and 515, all the radially expandable ends of fingers 22, 42, 522 and 542 are splayed into two spaced apart arrays that dilate sleeve 50 and the sleeve material extending between the two arrays. FIGS. 7-9 illustrate occluder catheter 910 having yet another occluder 915, which is similar to occluders 15 and 515, except that occluder 915 has only one expander, which has fingers 942 slidably aligned with deflector ring 60, instead of a mating expander. Deflector ring 60 is coupled to inner shaft 30'. Sliding the expander against deflector ring 60 forces fingers 942 to splay the radially expandable finger ends into a single array that dilates sleeve 50 into sealing engagement with the patient's vessel. Since the proximal and distal positions of the expander and deflector ring 60 may be reversed, then the conjoined, radially constrained finger ends may be referred to as first ends, and the radially expandable finger ends may be referred to as second finger ends.

Deflector ring 60 may be formed from a tube, and may have a chamfer on one end to receive and guide the tips of fingers 942 over the first step in diameter as the expander and ring 60 are slid against each other.

In an embodiment using deflector ring 60, such as occluder catheter 910, the fingers of the mating expander may be separated by thin slits instead of slots that are wide enough to receive interposing fingers of another expander. Without slots between the fingers, the single expander may have fingers that are wider than fingers that provide slots there between. Alternatively, as shown in FIGS. 7-9, fingers separated only by thin slits may be larger in number. By having fingers that are wider or larger in number, the single array of expanded finger ends may contact sleeve 50 with a greater total area, thus supporting better sealing contact between sleeve 50 and the vessel wall.

The embodiment shown in FIG. 7 depicts an expander having twelve expander fingers, and the embodiment shown in FIG. 4 depicts an expander having six expander fingers. It will be understood by skilled persons that the invention may be practiced with more or fewer than six expander fingers. The invention may also be practiced with more than twelve expander fingers.

It should be understood that the scope of the present invention is not to be limited by the illustrations for the foregoing description thereof, but rather by the appended claims, and certain variations and modifications of this invention will suggest themselves to one of ordinary skill in the art.

What is claimed is:

1. An occluder apparatus for use in a tubular vessel of a human body, the apparatus comprising:
    an elongate outer tube having a distal end;
    an elongate inner shaft having a distal end and extending slidably through the outer tube;
    an occluder comprising:
        a distal expander having a plurality of circumferentially spaced, longitudinally oriented fingers, the fingers having radially expandable proximal ends and radially constrained distal ends coupled to the inner shaft adjacent the inner shaft distal end;
        a proximal expander having a plurality of circumferentially spaced, longitudinally oriented fingers, the fingers having radially expandable distal ends and radially constrained proximal ends coupled to the outer tube adjacent the outer tube distal end, the fingers of the proximal expander being interposed in a slidable mating arrangement with the fingers of the distal expander wherein at least the fingers of the proximal expander slide over and against the radially constrained distal ends of the distal expander during transformation of the occluder between a collapsed configuration and a radially expanded configuration; and
        a flexible non-porous sleeve covering at least the fingers of both the distal and proximal expanders, wherein when the occluder is slidably transformed between the collapsed configuration and the expanded configuration, the radially expandable ends of the fingers of at least one of the expanders are radially splayed around the radially constrained ends of the fingers of the other expander to dilate the sleeve.

2. The occluder catheter of claim 1, wherein sliding the inner shaft within the outer tube effects relative longitudinal displacement of the distal and proximal expanders to cause transformation of the occluder between the expanded configuration and the collapsed configuration.

3. The occluder catheter of claim 1, wherein the inner shaft is selected from a group consisting of a core wire, a hollow shaft and a combination thereof.

4. The occluder catheter of claim 1, wherein the proximal expander is an integral portion of the outer tube.

5. The occluder catheter of claim 1, wherein the sleeve has two ends sealingly coupled about the catheter.

6. The occluder catheter of claim 1, wherein the non-porous sleeve comprises a material selected from a group consisting of a natural rubber, a synthetic rubber, a thermoplastic elastomer, a styrenic thermoplastic elastomer, a styrene-butylene-styrene, an inelastic thermoplastic, a polyester, a polyamide, a polyolefin, and a block co-polymer, a blend, a lamination, or a combination of the above materials.

7. The occluder catheter of claim 1, wherein, in the collapsed configuration, the radially expandable finger ends rest between the adjacent interposed fingers.

8. The occluder catheter of claim 1, wherein, on at least one of the expanders, the radially expandable finger ends are wider than the radially constrained finger ends.

9. The occluder catheter of claim 8, wherein, in the collapsed configuration, the wider finger ends rest upon the adjacent interposed fingers.

\* \* \* \* \*

UNITED STATES PATENT AND TRADEMARK OFFICE
CERTIFICATE OF CORRECTION

PATENT NO. : 7,597,703 B2  Page 1 of 1
APPLICATION NO. : 10/935851
DATED : October 6, 2009
INVENTOR(S) : Ghaleb A Sater It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 504 days.

Signed and Sealed this

Twenty-eighth Day of September, 2010

David J. Kappos
*Director of the United States Patent and Trademark Office*